(12) United States Patent
Brekke et al.

(10) Patent No.: US 7,463,801 B2
(45) Date of Patent: Dec. 9, 2008

(54) SIDE-FIRING LASER

(75) Inventors: John Paul Brekke, Cool, CA (US); Gregory G. Brucker, Minneapolis, MN (US)

(73) Assignee: Medical CV, Inc., Grove Heights, MN (US)

( * ) Notice: Subject to any disclaimer, the term of this patent is extended or adjusted under 35 U.S.C. 154(b) by 0 days.

(21) Appl. No.: 11/155,348

(22) Filed: Jun. 17, 2005

(65) Prior Publication Data

US 2006/0285793 A1 Dec. 21, 2006

(51) Int. Cl.
*G02B 6/42* (2006.01)
*G02B 6/26* (2006.01)
*G02B 6/00* (2006.01)

(52) U.S. Cl. ............................. 385/38; 385/18; 385/12

(58) Field of Classification Search .................. 385/38, 385/18, 12
See application file for complete search history.

(56) References Cited

U.S. PATENT DOCUMENTS

| | | | |
|---|---|---|---|
| 3,516,001 A * | 6/1970 | Ask et al. ...................... 372/6 |
| 4,209,017 A | 6/1980 | Shaw |
| 4,785,815 A | 11/1988 | Cohen |
| 5,233,677 A | 8/1993 | Winslow |
| 5,290,278 A | 3/1994 | Anderson |
| 5,343,543 A | 8/1994 | Novak, Jr. et al. |
| 5,428,699 A | 6/1995 | Pon |
| 5,487,740 A | 1/1996 | Sulek et al. |
| 5,495,541 A | 2/1996 | Murray et al. |
| 5,537,499 A * | 7/1996 | Brekke ........................ 385/31 |
| 5,571,099 A * | 11/1996 | Purcell et al. .................. 606/17 |
| 5,772,657 A * | 6/1998 | Hmelar et al. ................. 606/15 |
| 6,136,611 A * | 10/2000 | Saaski et al. ................. 436/527 |
| 6,263,133 B1 * | 7/2001 | Hamm ........................ 385/33 |
| 6,971,394 B2 | 12/2005 | Sliwa, Jr. et al. |
| 2005/0164131 A1 | 7/2005 | Yokouchi |
| 2005/0273090 A1* | 12/2005 | Nieman et al. ................. 606/15 |

(Continued)

FOREIGN PATENT DOCUMENTS

EP 0 073 617 A1 3/1983

(Continued)

OTHER PUBLICATIONS

"Ceramoptec®, Optran® HUV, Optran® HWF," CeramOptec Industries, Inc., 515A Shaker Road, East Longmeadow, Massachusetts, USA 01028, from website www.ceramoptec.com, 2 pages (May 2003).

(Continued)

*Primary Examiner*—Kianni C Kaveh
(74) *Attorney, Agent, or Firm*—Merchant & Gould, P.C.

(57) ABSTRACT

An apparatus for transmitting laser light and redirecting the light laterally relative to an axis of the apparatus includes an optical fiber having both a core and a cladding surrounding the core. The optical fiber terminates at a distal tip having a surface inclined relative to the axis of the optical fiber. A tubular member surrounds the optical fiber at its distal end. The distal end of the optical fiber has a portion opposing the tubular member for being united to the tubular member. The distal portion is joined to the tubular member by an intermediate material selected to have an index of refraction matching that of the core and the tubular member.

10 Claims, 3 Drawing Sheets

U.S. PATENT DOCUMENTS

2006/0009759 A1 1/2006 Chrisitian et al.
2006/0025762 A1 2/2006 Mohan et al.

FOREIGN PATENT DOCUMENTS

EP 0 422 233 A1 4/1991

OTHER PUBLICATIONS

"Special Optical Fiber Technologies, VIS/IR Quartz/Quartz Fibers," Fibertech USA, Inc., 4111 East Valley Auto Drive, Suite 104, Mesa, Arizona, USA 85206, from website www.us-fibertech.com, 3 pages (Jun. 27, 2005).

* cited by examiner

SIDE-FIRING LASER

I. BACKGROUND OF THE INVENTION

1. Field of the Invention

This invention pertains to optical fibers for discharging laser energy laterally to an axis of the optical fiber. More particularly, this invention pertains to such an optical fiber and a method for making the same.

2. Description of the Prior Art

So called "side-firing" optical fibers discharge light laterally or transverse to a longitudinal axis of the optical fiber as opposed to discharging light from a laser tip in a direction substantially parallel to the axis of the optical fiber. An example of a side-firing optical fiber is shown in U.S. Pat. No. 4,785,815 to Cohen dated Nov. 22, 1988. Particularly, FIGS. 7 and 9 of the '815 patent show optical fiber tips for discharging energy laterally relative to the axis of an optical fiber.

Optical fibers are fragile when not protected by appropriate cladding, jacket and buffers. Currently, the construction of a side-firing optical fiber requires removal of these components and addition of other materials, a process which can be difficult or expensive to manufacture in a manner which preserves the desired optical qualities while avoiding damage to a fragile optical fiber during the assembly process. A more simple construction of a side-firing optical fiber is disclosed in U.S. Pat. No. 5,537,499 to Brekke, dated Jul. 16, 1996. As shown in FIGS. 7-11 of the '499 patent, an optical fiber is placed within a tubular member formed of silica. The optical fiber has an inclined end surface within a gas filled chamber to cause reflection of light traveling along the axis of the optical fiber to exit the optical fiber tip transverse to the optical fiber axis. The optical fiber tip is fused to the silica of the tubular member to create a continuous material from the optical fiber tip through the silica tubular member to avoid alteration in an index of refraction throughout the light path.

While the design of the '499 patent is an efficient design for many applications, it has limitations. Specifically, the design of the '499 patent is limited to a optical fiber having a cladding which can withstand the thermal energies required during the process of fusing the optical fiber tip to the silica tubular member. The fusion process results in a melting of the optical fiber in the silica tubular member to form a continuous material. This occurs at the melting point of fused silica, a temperature of about 1470° C. If the cladding of the optical fiber cannot withstand such temperatures, the cladding will melt resulting in at least a portion of the length of the optical fiber being unclad and thereby not reflective to incident internal energy. In the '499 patent, such cladding is a so-called "doped fused silica cladding" which can withstand the temperatures of the welding process of the optical fiber tip to the silica tubular member.

Optical fibers having doped fused silica cladding are acceptable for many applications. For most optical fibers, the doped fused silica layer is approximately 20 microns thick. There is only a small index of refraction difference between the fused silica core of the optical fiber and the doped fused silica cladding. The critical angle of an optical fiber is determined by the index of refraction difference between its core and cladding. The critical angle is defined as the maximum incidence angle from the centerline of an optical fiber for total internal reflection. The smaller the index of refraction difference between the core and cladding, the more collinear the laser light must be when entering the optical fiber. For most commercially available optical fibers using a fused silica core and a doped fused silica cladding, the critical angle of the optical fiber must be less than 13 degrees. A critical angle of less than 13 degrees corresponds to a numerical aperture of 0.22 (which is approximately the arcsine of the critical angle). Many commercially available flash lamp lasers have very small divergence angles are ideally suited for use with the design of the '499 patent having doped silica cladding on a silica core optical fiber.

In addition to so-called flash lamp lasers, diode lasers are becoming increasingly popular due to their lower cost, smaller physical size and greater reliability. However, diode lasers are significantly constrained as to power output, minimum spot size and divergence angle. As a result, applications using diode lasers need optical fibers for delivering the laser energy which maintain high optical efficiency to provide adequate power to the optical fiber tip and accept a divergent beam significantly greater than commercially available side firing optical fibers which use optically efficient designs such as the '499 patent.

Commonly, the divergence angle of most diode lasers is approximately 22 degrees which requires an optical fiber with a numerical aperture of 0.37 to capture and retain all incident energy. This is significantly greater than the maximum tolerable numerical aperture of commercially available fibers which use a design such as that of the '499 patent containing a silica core optical fiber with a doped fused silica cladding. Accordingly, the use of such a diode laser with such a design results in a substantial loss of power during transmission of the laser energy along the optical fiber because the incidence angle of the laser is larger than the critical angle of the optical fiber.

A higher numerical aperture would be possible with the design of the '499 patent if the doped silica cladding were to be replaced with any one of a number of different commercially available plastic claddings having a higher index of refraction difference between the cladding and the silica core of the optical fiber. Unfortunately, such plastic claddings have melting temperatures significantly lower than that of the silica core. As a result, the fusion process described in the '499 patent cannot be used with such optical fibers since, during the fusion process, a substantial length of the plastic cladding will melt leaving a substantial length of the optical fiber core unclad. This substantial length results in loss of laser energy. Since laser diodes already operate at relatively low power outputs, such a loss of energy is unacceptable for most applications.

It is an object of the present invention to provide an optical fiber having the advantages of the '499 patent while avoiding the aforementioned disadvantages.

II. SUMMARY OF THE INVENTION

According to a preferred embodiment of the present invention, an apparatus is disclosed for transmitting laser light and redirecting the light laterally relative to an axis of the apparatus. The apparatus includes an optical fiber having both a core and a cladding surrounding the core. The optical fiber terminates at a distal tip which includes a surface inclined relative to the axis of the optical fiber within a gas filled chamber. A silica tubular member surrounds the optical fiber at its distal end. The distal end of the optical fiber has a portion opposing the silica tubular member for being united to the silica tubular member. The distal portion is joined to the silica tubular member by an intermediate material selected to have an index of refraction matching that of the core and the silica tubular member.

III. BRIEF DESCRIPTION OF THE DRAWINGS

FIG. 1 is the view of FIG. 10 of U.S. Pat. No. 5,573,499 showing, in lateral cross section, an optical fiber fused to a surrounding tube, according to the teachings of the '499 patent;

FIG. 2 corresponds to FIG. 11 of the '499 patent and is a view taken generally along lines 2-2 of FIG. 1;

Figure 4:
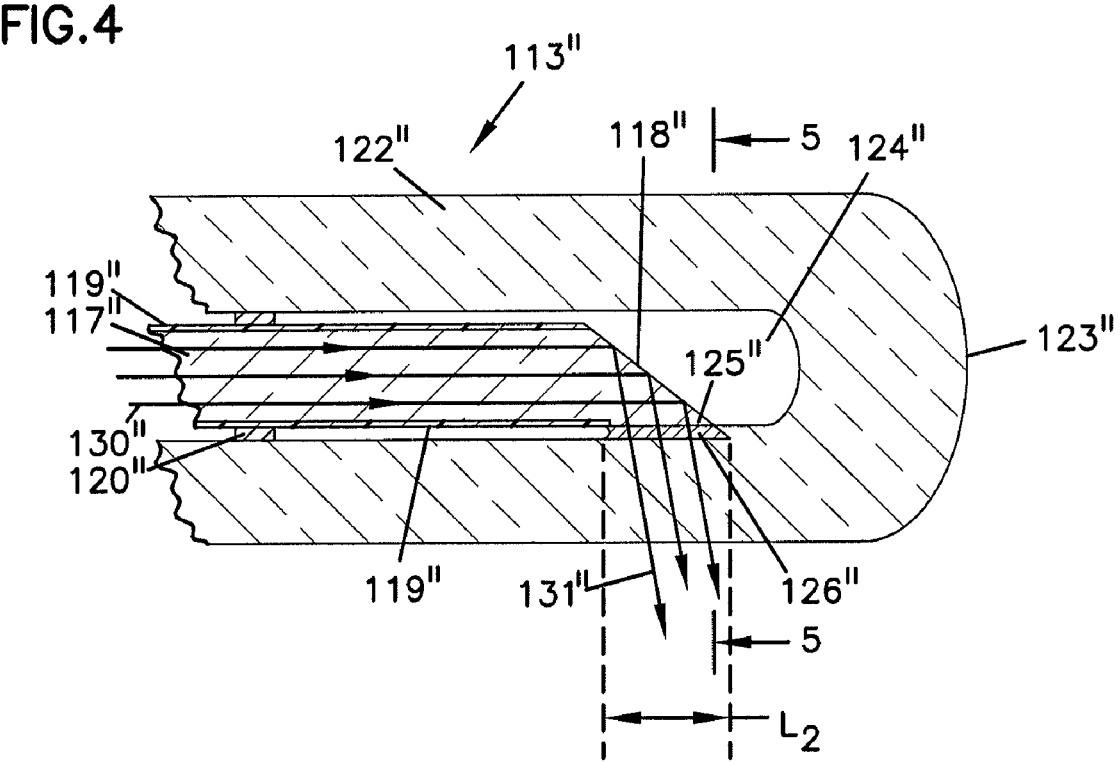
FIG. 4 is a view similar to that of FIG. 1 and showing an improvement in a manufacturing process according to the present invention.
Figure 6:
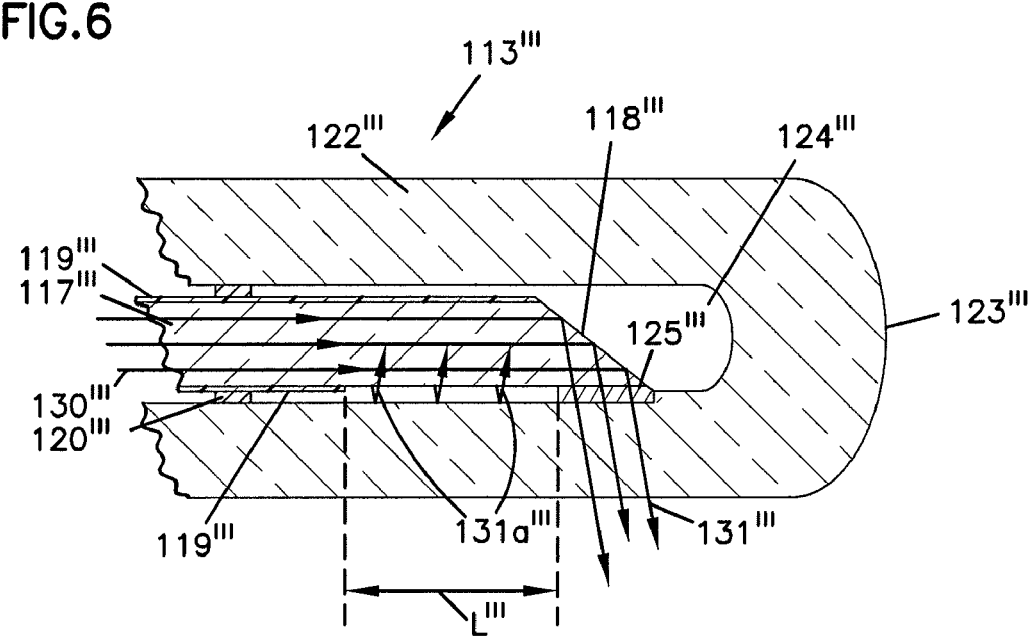
Figure 7:
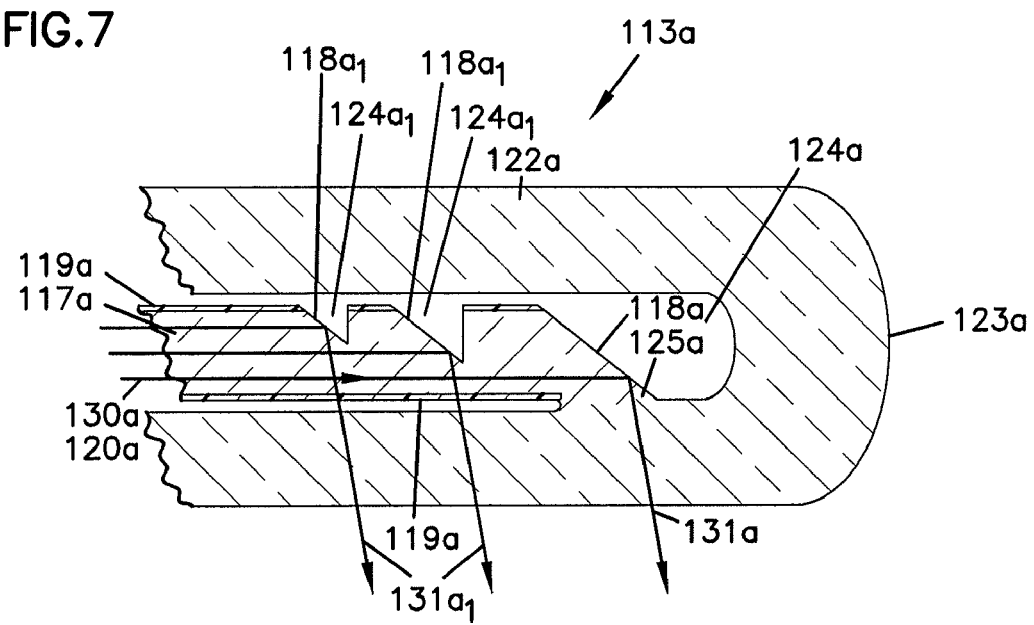

FIG. 6 is a view similar to that of FIG. 4 showing an alternative embodiment of the present invention which uses a plastic clad optical fiber and a thermal bond with a cap having substantially the same index of refraction as the cladding of the optical fiber; and FIG. 7 is a view similar to that of FIG. 4 showing a still further alternative embodiment of the present invention adapted to create a linear pattern of light energy from a distal end of a fiber.

IV. DETAILED DESCRIPTION OF THE PREFERRED EMBODIMENT

With reference now to the various drawing figures in which identical elements are numbered identically throughout, a description of a preferred embodiment of the present invention will now be provided. The complete disclosure including the specification and drawings of U.S. Pat. No. 5,537,499, to Brekke issued Jul. 16, 1996, is incorporated herein by reference as though set forth in full.

A. Teachings of the Prior Art

Figure 1:
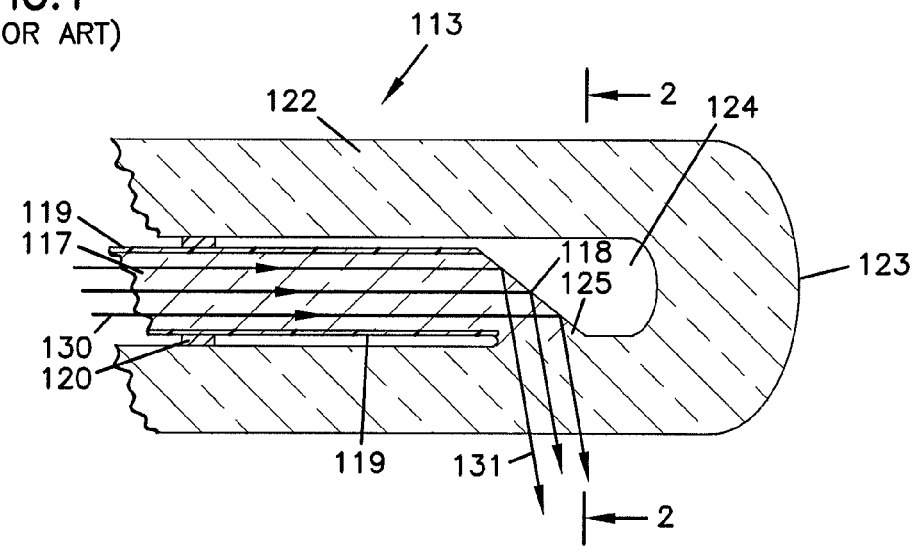
Figure 2:
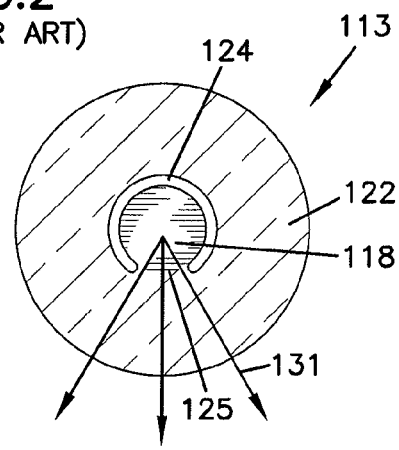

In order to facilitate an understanding of the present invention, an initial description will be presented of a prior art optical fiber combination as taught in U.S. Pat. No. 5,537, 499. FIGS. 1 and 2 are reproductions of Figures of 10 and 11 of the '499 patent. The figures show a side firing laser optical fiber apparatus 113.

The apparatus 113 has an elongated flexible optical fiber 117 terminating at an inclined end surface 118. The optical fiber 117 has a silica optical fiber core surrounded with a doped fused silica cladding 119. A sleeve 120 of plastic material covers the cladding 119. It will be noted that the sleeve 120 is spaced from the end surface 118.

The cladding 119 is enclosed within a jacket (not shown) of plastic material, such as Teflon. The surface 118 has a generally oval polished shape. According to the '499 patent, a diamond-tipped abrasive tool, a carbon dioxide laser tightly focused or excimer laser can be used to polish the surface 118.

The surface 118 is inclined forwardly at an angle 37° relative to the longitudinal axis of the optical fiber 117. Such angle can be between 37 to 45° relative to the longitudinal axis of the optical fiber 117, or such other angles as may be suitable for a particular application. When the angle of the surface 118 is 37°, reflected light will emerge at approximately 70° in air with an associated divergence.

A tubular layer of silica cladding 119 surrounds the core of the optical fiber 117 to protect the core and maintain the laser light within the optical fiber 117. A transparent capsule of tubular member 122 of silica having a closed convex curved end 123 is located about the distal end of the optical fiber 117 to enclose the distal end of the optical fiber within an air chamber 124. The distal end of the optical fiber 117 is surrounded by air chamber 124. Member 122 is a silica cylindrical tubular member made of silica material the same as or similar to the silica material of optical fiber 117.

The distal end of optical fiber 117 is united at 125 to the adjacent inside wall of silica tubular member 122. The silica materials of optical fiber 117 and tubular member 122 are fused with localized heat. As shown in FIG. 7 of the '499 patent, the heat required to cause the fusion of the silica materials of optical fiber 117 and tubular member 122 is in the range of 1400° C. to 1700° C.

As described in the '499 patent, a laser beam is directed through an optical lens which concentrates the laser beam on the surface of silica tubular member 122. The heat from the laser beam is conducted through the silica of tubular member 122 toward the distal end of optical fiber 117. The high temperature heat radiates across the air gap and melts the silica of the optical fiber core as well as the silica of tubular member 122. The opposing silica materials of optical fiber 117 and tubular member 122 are melted and fused together as shown in FIGS. 8-11 of the '499 patent.

Referring to FIGS. 1 and 2 (which correspond to FIGS. 10 and 11 of the '499 patent), light or laser beam 130 generated by a laser axially propagates down optical fiber 117. When light 130 encounters a change in refractive index, it laterally redirects the light energy indicated by arrows 131. The angle of polished surface 118 being 37 degrees relative to the longitudinal axis of optical fiber 117 results in almost total internal reflection of light 130 as redirected light 131 at an angle of approximately 70 degrees relative to the longitudinal axis of optical fiber 117.

Light 131 is efficiently redirected laterally through the distal end of optical fiber 117, the fused area 125 and silica tubular member 122. Optical fiber 117, fused area 125 and silica tubular member 122, being of the same silica materials, do not produce changes in the refractive indices and thereby do not produce reflected light nor secondary light.

B. Limitations of the Prior Art Design

As previously described, the construction of FIGS. 1 and 2 are necessarily limited to use with lasers having a numerical aperture of 0.22 or less. For use with diode lasers (having a numerical aperture of 0.37 or greater), the doped silica cladding 119 can not be used since too great of a power loss occurs as a result of transmission loss of the energy along the optical fiber escaping through to the cladding 119.

Plastic claddings provide the necessary cladding for such an energy source. Examples of such plastic claddings are Ceramoptec Optran HUV/of CeramOptec Industries, Inc., 515A Shaker Road, East Longmeadow, Mass., USA 01028 (www.ceramoptec.com) and FiberTech VIS/IR of Fibertech USA, Inc., 4111 East Valley Auto Drive, Suite 104, Mesa, Ariz., USA 85206 (www.us-fibertech.com). However, plastic claddings have a substantially lower melting temperature (about 85° C.) than silica. This precludes their efficient use in the manufacturing process described with reference to FIGS. 1 and 2.

Figure 3:
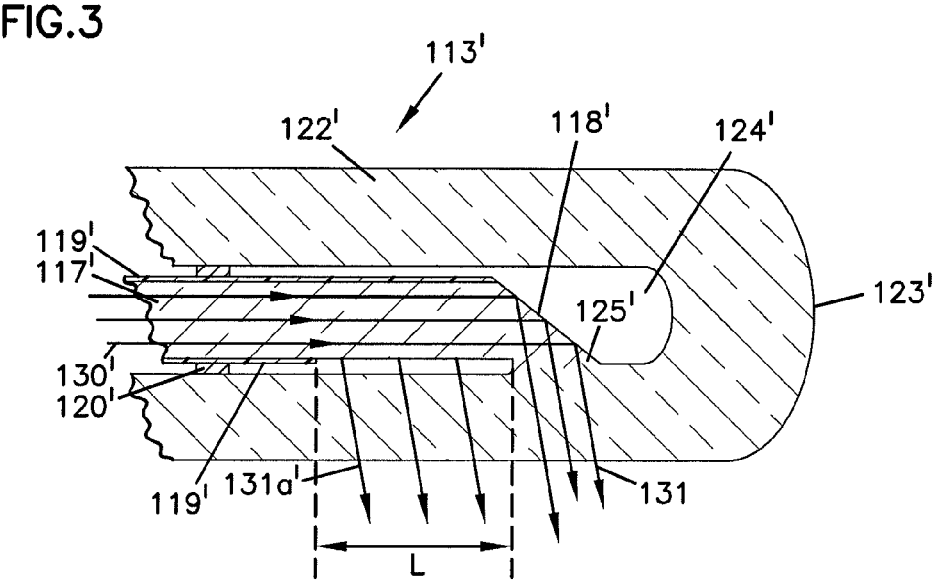
FIG. 3 is the view of FIG. 1 showing energy loss resulting from partial destruction of a cladding of a optical fiber of FIG. 1.

This disadvantage is shown with reference to FIG. 3. In FIG. 3, all elements in common with those of FIGS. 1 and 2 are numbered identically with the addition of an apostrophe to distinguish the embodiments. Accordingly, not all elements will be separately described except to the extent they different from those in FIGS. 1 and 2.

FIG. 3 illustrates the optical fiber 117' identical to the optical fiber 117, except that the cladding 119' is a plastic cladding. A representative example of such a cladding is the afore-mentioned FiberTech VIS/IR with a hard polymer cladding with a melting point of 85° C.

With a plastic cladding, the optical fiber 117' may efficiently transport laser energy from a diode laser and having a numerical aperture of 0.37. However, during the fusion process described with reference to FIGS. 1 and 2, the cladding 119' in close proximity to the fused area 125' will melt exposing a length L of the cylindrical wall of the optical fiber core 117'. Due to such exposure, light 131a' exits the core prematurely, resulting is a substantial power loss. With lower power diode lasers, such a power loss is unacceptable for most commercial applications.

C. Improvement of the Present Invention

Figure 5:
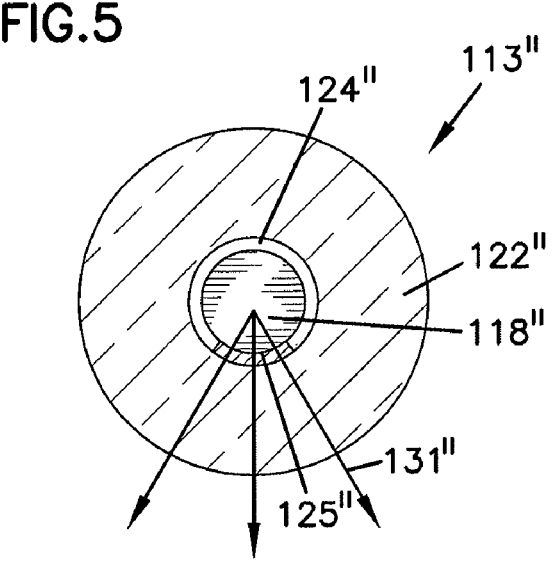
FIG. 5 is a view taken along line 5-5 of FIG. 4.

The design limitations of FIGS. 1-3 are overcome with the present invention, as will now be described with reference to FIGS. 4 and 5. In FIGS. 4 and 5, all elements in common with those of the previously described embodiments are numbered identically within the addition of a double apostrophe to distinguish the embodiments and are not separately described except as necessary to distinguish the embodiments.

An optical fiber 117" of silica core is provided with a plastic cladding 119" such as FiberTech VIS/IR. The plastic cladding 119" on the silica core 117" provides efficient transport of laser energy with a numerical aperture of 0.37 or greater. This permits efficient use of the apparatus 113" with a diode laser energy source.

The optical fiber 117" is surrounded by a silica tubular member 122" with a silica cap 123" to surround the inclined surface 118" of the optical fiber distal end with an air chamber 124". At the end portion of the wall of the optical fiber 117" (i.e., at the intersection of the optical fiber wall and inclined surface 118" near the acute angled point of the inclined surface 118"), a portion of the cladding 119" is removed along a length $L_2$. The portion of the optical fiber wall along the length $L_2$ faces an opposing surface of the silica tubular member 122".

An adhesive layer 126" is positioned between the wall of the optical fiber 117" and the silica tubular member 122" along length $L_2$. The reminder of the cladding 119" extends up to the adhesive layer 126".

The adhesive layer 126" is selected to have an index of refraction which matches the index of refraction of the optical fiber core 117" and the silica tubular member 122". As a result, there is little or no power loss for light passing through between the core 117" and the adhesive 126" or between the adhesive 126" and the tubular member 122". Adhesives 126" having an index of refraction to match the silica of the core 117" and the silica tubular member 122" are commercially available. An example of such is Optocast™ 3580 adhesive by Electronic Materials Inc., 1814 Airport Road, Breckenridge, Colo., USA, 80424.

It will be noted that by using an index-matching adhesive 126", index matching is made between the optical fiber 117" and the tubing 122" in a manner to obtain the benefits of the fusion of the prior art, but avoiding a process requiring application of heat. By avoiding application of heat, the cladding 119" is not destroyed by thermal energy, and remains intact throughout the length of the optical fiber 117" and up to and abutting the adhesive layer 126". As a result, there is little or no loss of scattered light through the wall of the optical fiber 117" as described with reference to FIG. 3. Manufacturing efficiencies associated with the prior art of FIGS. 1 and 2 can be achieved as well as providing for an optical fiber of plastic cladding 119", which can accommodate a much greater numerical aperture than that limited by the doped silica cladding of the prior art.

FIG. 6 illustrates an embodiment to permit use of the manufacturing process of U.S. Pat. No. 5,537,499, to Brekke but avoiding the premature loss of energy due to melting of a plastic cladding. In FIG. 6, elements in common with previously described embodiments are numbered identically with the addition of three apostrophes to distinguish the embodiments. To the extent those elements materially differ from previous embodiments in structure, materials or method of manufacture, they are separately described in the following description of FIG. 6. Otherwise, no additional description is necessary.

In FIG. 6, an optical fiber 117''' of silica core is provided with a plastic cladding 119''' such as FiberTech VIS/IR as previously described. Instead of surrounding the fiber 117''' with a silica tubular member and a silica cap as previously described, the fiber 117''' is surrounded by a silica tubular member 122''' and a silica cap 123'''. The silica tubular member 122''' and cap 123''' are formed from a doped fused silica having an index of refraction substantially identical to the index of refraction of the cladding 119'''.

In the embodiment of FIG. 6, the fiber end is not adhered to the silica tubular member using an adhesive as described with reference to the embodiments shown in FIGS. 4 and 5. Instead, the doped fused silica tubular member 122" is fused and bonded to the fiber 117''' at 125''' as described in U.S. Pat. No. 5,537,499 to Brekke. The reference numeral 125''' illustrates area of welding the material of the fiber core 117''' and the silica tubular member 122". During this fusion, any cladding material in the area melts and evaporates and does not materially comprise part of the material of area 125'''. This fusion process partially melts the plastic cladding 119''' (as described with reference to FIG. 3) leaving an unclad length L'''. Light 131a''' which escapes the fiber 117''' along length L''' is reflected back into the fiber 117".

In FIG. 6, where the cladding 119''' along length L''' has been destroyed by the heat but proximal to the beginning of the angled surface 118''' of the optical fiber, the light 131a''' will be reflected back toward the center of the fiber 117''' because the incidence angle of the light 131a''' at the silica tubular member 122''' is less than the critical angle. Once the light hits the angled surface 118''' and is reflected toward the side of the optical fiber, the incidence angle is greater than the critical angle and the light 131''' passes out the fiber.

FIG. 7 illustrates a still further alternative embodiment of the present adapted to create a linear pattern of light energy from a distal end of a fiber. In FIG. 7, elements in common with FIGS. 1 and 2 are numbered identically with the addition of "a" to distinguish the embodiments. To the extent those elements materially differ from previous embodiments in structure, materials or method of manufacture, they are separately described in the following description of FIG. 7. Otherwise, no additional description is necessary.

The embodiment of FIG. 7 illustrates a fiber manufactured with the thermal fusion process of U.S. Pat. No. 5,537,499 to Brekke. It will be appreciated the novel structure of FIG. 7 could be incorporated into a fiber manufactured according to the embodiment described with reference to FIGS. 4 and 5.

In FIG. 7, multiple sloped surfaces $118a_1$ are formed in the core 117a proximal to the sloped surface 118a. The sloped surfaces $118a_1$ are formed by creating notches in the fiber. The sloped surfaces $118a_1$ are bounded by air layers $124a_1$. The sloped surfaces $118a_1$ have the same angle to the fiber axis as the distal inclined surface 118a. Therefore light $131a_1$ exits the fiber 117a from the sloped surfaces $118a_1$ at the same angle as light 131a from inclined surface 118a. Since this light 131a passes the cladding at an angle greater than a critical angle of the cladding 119a, the light 131a₁ is not reflected back into the fiber 117a.

The above specification, examples and data provide a complete description of the manufacture and use of the composition of the invention. Since many embodiments of the invention can be made without departing from the spirit and scope of the invention, the invention resides in the claims hereinafter appended.

We claim:

1. An apparatus for transmitting laser light and redirecting the light laterally relative to the apparatus comprising:
    an optical fiber having a core and a cladding surrounding a sidewall of the core, the optical fiber having a distal end section terminating at a forwardly inclined surface;
    the cladding being a polymeric material having a melting temperature substantially lower than a melting temperature of the core;
    a tubular member surrounding the distal end section of the optical fiber, the tubular member having a closed end to confine the distal end section and inclined surface;
    the sidewall of the distal end section of the core having a portion thereof generally opposite the inclined surface and with the cladding removed from the portion to define an exposed and unclad portion of the core;
    the exposed and unclad portion of the core united to an opposing portion of the tubular member;
    the exposed and unclad portion of the core and the opposing portion of the tubular member being joined together at an intermediate material selected to have an index of refraction matching with the core and the tubular member;
    whereby light from a laser propagated down the optical fiber is redirected laterally from the inclined surface through the united exposed and unclad portion of the core and the opposing portion of the tubular member.

2. An apparatus according to claim 1 wherein the intermediate material is an index-matching adhesive.

3. An apparatus according to claim 2 wherein the apparatus is formed by removing the cladding to define the unclad portion before applying the adhesive.

4. An apparatus according to claim 2 wherein a remainder of the fiber sidewall adjacent the unclad region has an intact cladding.

5. An apparatus according to claim 1 wherein said cladding has a numerical aperture greater than 0.22.

6. An apparatus according to claim 1 wherein the cladding has a numerical aperture of at least about 0.37.

7. An apparatus according to claim 1 wherein the tubular member is a doped fused silica having an index of refraction approximately the same as that of the cladding.

8. An apparatus according to claim 7 wherein the intermediate material is a thermally fused region of the unclad portion of the core and the opposing portion of the tubular member.

9. An apparatus according to claim 8 wherein the cladding is removed during formation of the thermally fusing region.

10. An apparatus according to claim 9 wherein a cladding of the sidewall outside of the region is removed during formation of the thermally fusing region.

\* \* \* \* \*